(12) United States Patent
Okoniewski

(10) Patent No.: US 9,308,021 B2
(45) Date of Patent: Apr. 12, 2016

(54) EXPANDING SURGICAL ACCESS PORT

(71) Applicant: Covidien LP, Mansfield, MA (US)

(72) Inventor: Gregory Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/517,971

(22) Filed: Oct. 20, 2014

(65) Prior Publication Data
US 2015/0038796 A1 Feb. 5, 2015

Related U.S. Application Data

(62) Division of application No. 13/343,813, filed on Jan. 5, 2012, now Pat. No. 8,888,691.

(60) Provisional application No. 61/435,442, filed on Jan. 24, 2011.

(51) Int. Cl.
*A61B 1/32* (2006.01)
*A61B 17/34* (2006.01)
*A61B 17/00* (2006.01)

(52) U.S. Cl.
CPC ......... *A61B 17/3423* (2013.01); *A61B 17/3431* (2013.01); *A61B 17/3462* (2013.01); *A61B 2017/00539* (2013.01); *A61B 2017/3429* (2013.01); *A61B 2017/3445* (2013.01)

(58) Field of Classification Search
CPC ................. A61M 29/02; A61M 29/00; A61B 17/12136; A61B 17/12022; A61B 17/12109; A61B 2017/1205; A61B 17/00234

USPC ............................ 600/201–210; 606/190–194
See application file for complete search history.

(56) References Cited

U.S. PATENT DOCUMENTS

| | | | |
|---|---|---|---|
| 5,366,478 A | 11/1994 | Brinkerhoff et al. |
| 5,524,644 A | 6/1996 | Crook |
| 5,803,921 A | 9/1998 | Bonadio |
| 5,906,577 A | 5/1999 | Beane et al. |
| 5,964,781 A | 10/1999 | Mollenauer et al. |
| 6,033,428 A | 3/2000 | Sardella |

(Continued)

FOREIGN PATENT DOCUMENTS

| EP | 2044889 A1 | 4/2009 |
|---|---|---|
| EP | 2179699 A1 | 4/2010 |

(Continued)

OTHER PUBLICATIONS

European Search Report from EP Application No. EP12152164 mailed Apr. 19, 2012.

(Continued)

*Primary Examiner* — Todd E Manahan
*Assistant Examiner* — Tara R Carter

(57) ABSTRACT

A surgical access port that includes a cylindrical member having a proximal end and a distal end and defining a longitudinal axis; at least two lumen extending through the cylindrical member along the longitudinal axis; at least one cavity defined in the cylindrical member and positioned radially within the at least two lumen; and a source of inflation fluid coupled to the at least one cavity, the source of inflation configured to permit selectable inflation of the at least one cavity, whereby inflation of the at least one cavity increases the radial distance between the at least two lumen.

7 Claims, 4 Drawing Sheets

(56) References Cited

U.S. PATENT DOCUMENTS

| | | |
|---|---|---|
| 6,332,468 B1 | 12/2001 | Benetti |
| 6,454,783 B1 | 9/2002 | Piskun |
| 6,972,026 B1 | 12/2005 | Caldwell et al. |
| 7,850,600 B1 | 12/2010 | Piskun |
| 8,888,691 B2 | 11/2014 | Okoniewski |
| 2002/0072762 A1 | 6/2002 | Bonadio et al. |
| 2003/0014076 A1* | 1/2003 | Mollenauer et al. ........ 606/213 |
| 2008/0027476 A1 | 1/2008 | Piskun |
| 2008/0033344 A1 | 2/2008 | Mantell |
| 2008/0081951 A1* | 4/2008 | Frasier et al. ............... 600/207 |
| 2009/0093752 A1 | 4/2009 | Richard et al. |
| 2009/0221966 A1 | 9/2009 | Richard |
| 2010/0100043 A1 | 4/2010 | Racenet |
| 2010/0249524 A1 | 9/2010 | Ransden et al. |
| 2010/0312065 A1 | 12/2010 | Shelton, IV et al. |
| 2011/0082341 A1 | 4/2011 | Kleyman et al. |
| 2011/0166423 A1* | 7/2011 | Farascioni et al. ........... 600/208 |

FOREIGN PATENT DOCUMENTS

| | | |
|---|---|---|
| EP | 2289438 A1 | 3/2011 |
| EP | 2343019 | 7/2011 |
| WO | 00/54675 | 9/2000 |
| WO | 03/034908 A2 | 5/2003 |
| WO | 2005089655 A1 | 9/2005 |

OTHER PUBLICATIONS

European Search Report for corresponding EP1215218 date of mailing is Apr. 12, 2012 (7 pgs).

* cited by examiner

EXPANDING SURGICAL ACCESS PORT

CROSS-REFERENCE TO RELATED APPLICATIONS

This application is a divisional of U.S. patent application Ser. No. 13/343,813 filed Jan. 5, 2012, now U.S. Pat. No. 8,888,691, which claims benefit of U.S. Provisional Application No. 61/435,442 filed Jan. 24, 2011, and the disclosures of each of the above-identified applications are hereby incorporated by reference in their entirety.

BACKGROUND

1. Technical Field

The present disclosure relates to an access port for use in minimally invasive surgical procedures, such as endoscopic or laparoscopic-type procedures, and more particularly to an expanding surgical access port for use in minimally invasive procedures.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures. During a typical minimally invasive procedure, surgical objects, such as surgical access ports (e.g., trocar and/or cannula assemblies), endoscopes, or other instruments, are inserted into the patient's body through the incision in tissue. Prior to the introduction of the surgical object into the patient' body, insufflation gasses may be used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various access members are used during the course of minimally invasive procedures and are widely known in the art. A continuing need exists for an access member of a universal size that can be inserted into a variety of tissue incision sites and expands to fit such a variety of larger tissue incision sites. It is desirable to accommodate a variety of tissue incisions, and adapt to changing conditions at the surgery site.

SUMMARY

In accordance with various embodiments, the present disclosure is directed toward a surgical access port having at least one internal inflation cavity. The internal inflation cavity is capable of receiving and retaining fluid such that the internal inflation cavity, and thus the size of the surgical access port as a whole, increases under supplied inflation fluid. This increase is desirable to cause a more substantial seal between the surgical access port walls and the incision site, thereby maintaining the insufflated workspace. The surgical access port may additionally be capable of both radial and axial expansion under supplied inflation fluid.

The inflation cavity is internal to a cylindrical body that generally has an hourglass shape, defines a longitudinal axis, and is coupled to a source of inflation fluid. In use, the operator of the surgical access port supplies inflation fluid from the source of inflation fluid, and the internal inflation cavity, and consequently, the body of the surgical access port expands in response to the supplied fluid. The driving force of the inflation fluid may be provided by a pump, reservoir, or any other suitable pressure-generating device. The internal inflation cavity is coupled to the source of inflation fluid through the use of an inflation coupling that provides a substantially fluid-tight seal between the internal inflation cavity and the source of inflation fluid.

The cylindrical body is formed of a material capable of both expansion and contraction. In embodiments, this material may be foam, or any other biocompatible material that is flexible in both radial and axial directions, yet resilient enough to resist deformation under the stress of the walls of an incision site. The cylindrical body has a proximal and a distal end, both substantially perpendicular to the longitudinal axis.

Disposed within, and extending through the cylindrical body along the longitudinal axis, is at least one lumen. The lumen provides a path from the proximal end of the surgical access port, through the cylindrical body, to the distal end of the surgical access port. The lumen or lumens may also change relative positioning with each other and other components of the surgical access port in response to expansion from supplied inflation fluid. Specifically, the lateral spacing between lumens with respect to the longitudinal axis will change in response to expansion of the surgical access port under supplied inflation fluid. By virtue of the flexible and compressible nature of the cylindrical body, lumen diameter may be reduced as a result of the expansion of the cylindrical body, and a tighter seal may form about an instrument disposed within a lumen. Additionally, the lumens may alter their path in response to deflection of an inserted instrument relative to the longitudinal axis.

Also provided is a method for accessing an internal body cavity. The method includes the steps of positioning the surgical access port in an internal body cavity, expanding the surgical access port to a desired size with fluid from the source of inflation fluid, and accessing the internal body cavity via the surgical access port. The surgical access port allows the passage of surgical tools and other devices into the body cavity. Removal of the device involves contracting the surgical access port such that it decreases in size so to allow generally unobstructed removal from an incision site.

DETAILED DESCRIPTION OF EMBODIMENTS

Figure 1:
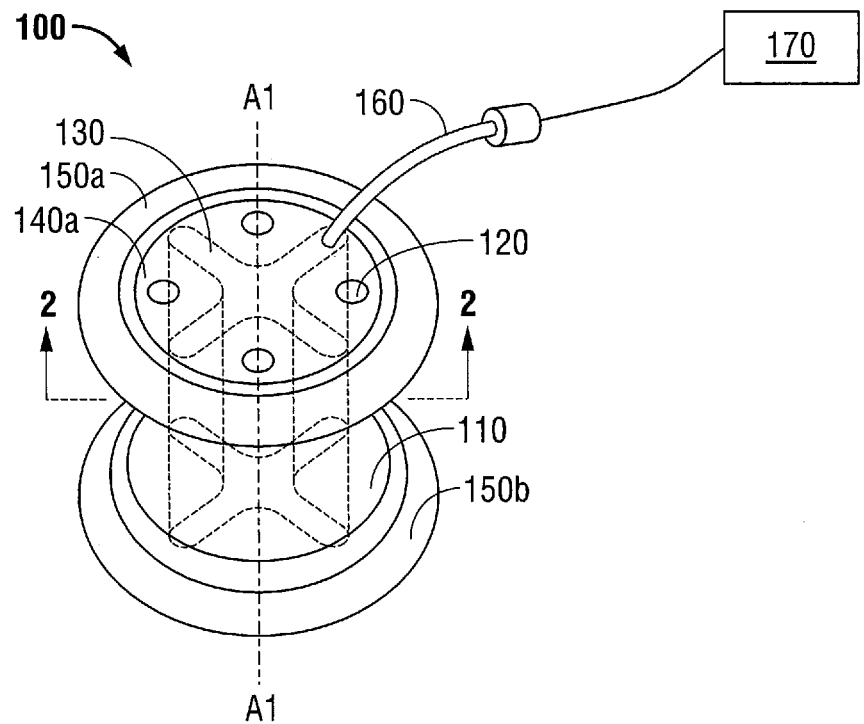
FIG. 1 is a top perspective view of a surgical access port containing four lumens, a central internal inflation cavity, and an inflation coupling.

The present disclosure will now describe in detail embodiments of a surgical access port with reference to the drawings in which like reference numerals designate identical or substantially similar parts in each view. Throughout the description, the term "proximal" will refer to the portion of the assembly closest to the operator, whereas the term "distal" will refer to the portion of the assembly farthest from the operator. Although discussed in terms of an incision for a minimally invasive procedure, the presently disclosed surgical access port may be used in any naturally occurring orifice (e.g. mouth, anus, or vagina).

Referring initially to FIG. 1, a surgical access port 100 is shown. The surgical access port 100 includes a cylindrical member 110 having a generally hourglass shape, a proximal end 140a and a distal end 140b, and defining a longitudinal axis A1. The proximal end 140a and the distal end 140b are substantially perpendicular to the longitudinal axis A1 and are each surrounded by an outer rim 150a and 150b, respectively. Extending through the cylindrical member 110 along the longitudinal axis A1 is at least one lumen 120, and in embodiments, a plurality of lumens 120. An example of an access port is disclosed in U.S. Patent Application Publication No. 2010/0240960 A1, the entire disclosure of which is incorporated by reference herein.

Also within the cylindrical member 110, separate from the lumens 120, is an internal inflation cavity 130. The internal inflation cavity 130 may be symmetrical and centrally disposed as shown here, but in embodiments, may be of shape, plurality, and placement so as to maximize its effect on the surrounding lumens 120. In embodiments, internal inflation cavity 130 may be of a generally "X" shape, with rounded edges. The internal inflation cavity 130 extends from some distance along the longitudinal axis A1 from the proximal end 140a of the cylindrical member 110, and terminates at some distance along the longitudinal axis A1 before the distal end 140b of the cylindrical member 110.

Coupled to the internal inflation cavity 130 is an inflation coupling 160, which may be in the form of a tube or a port configured to be attached to the source of inflation fluid 170. The inflation coupling 160 is coupled on its distal end to the internal inflation cavity 130, and on its proximal end to a source of inflation fluid 170. The internal inflation cavity 130 will be capable of retaining the inflation fluid. To this end, the internal inflation cavity 130 or the inflation coupling 160 may incorporate a structure to control the flow of inflation fluid to the internal inflation cavity. This structure may be a ball valve or other suitable flow control. Additionally, the inflation coupling 160 may contain a structure to contribute to maintaining a substantially fluid-tight seal with the surgical access port 100. Such structure may be a press-fit member, bayonet-type, or threaded configuration.

The source of inflation fluid 170 may be any source capable of supplying the inflation fluid to the internal inflation cavity 160. Such a capable source may be a syringe, pump, or reservoir. The source of inflation fluid 170 will supply inflation fluid that is biocompatible and suitable for surgical procedures, such as $CO_2$, air, or saline.

Figure 4:
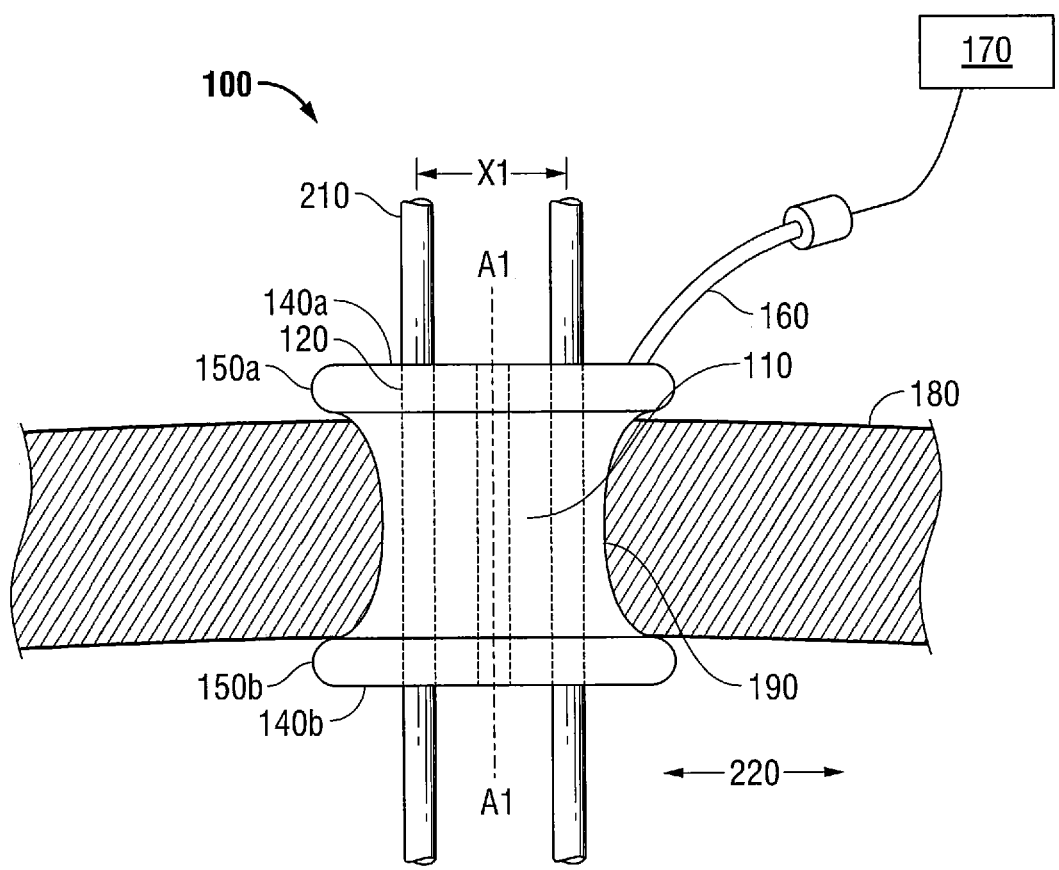
FIG. 4 is a side view of the surgical access port of FIG. 1, as shown in FIG. 3 with two instruments disposed therethrough.

In embodiments, a surgical access port 100 may also include a port for the communication of insufflation fluid to an internal body cavity 220 (see FIG. 4). Alternatively, one of the lumens 120 may communicate the insufflation fluid to the internal body cavity 220.

Figure 2:
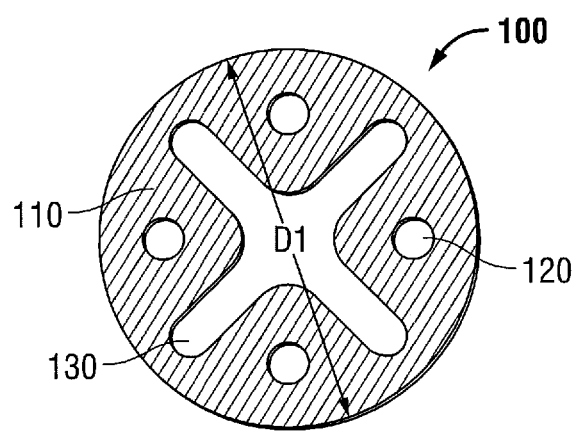
FIG. 2 is top plan cross-sectional view along the line 2-2 of the surgical access port of FIG. 1, showing four lumens, a central internal inflation cavity, and a first state diameter.

Turning to FIG. 2, the surgical access port 100 is shown in cross section along section line 2-2. In this view, each of the lumens 120 can be seen disposed radially about the internal inflation cavity 130. The lumens 120 are placed such that an expansion of the inflation cavity 130 will cause a shifting in the relative placement of the lumens 120. Such a shifting may allow greater dexterity and range in performing a surgical procedure with instruments 210 (see FIG. 3) disposed within the lumens 120. When the inflation cavity 130 is not inflated, as shown here, a first state is defined. In a first state, the inflation cavity 130 has an internal pressure that is essentially equalized with that of the surrounding environment. A first state diameter D1 is associated with the first state, measured transverse to the longitudinal axis A1.

Figure 3:
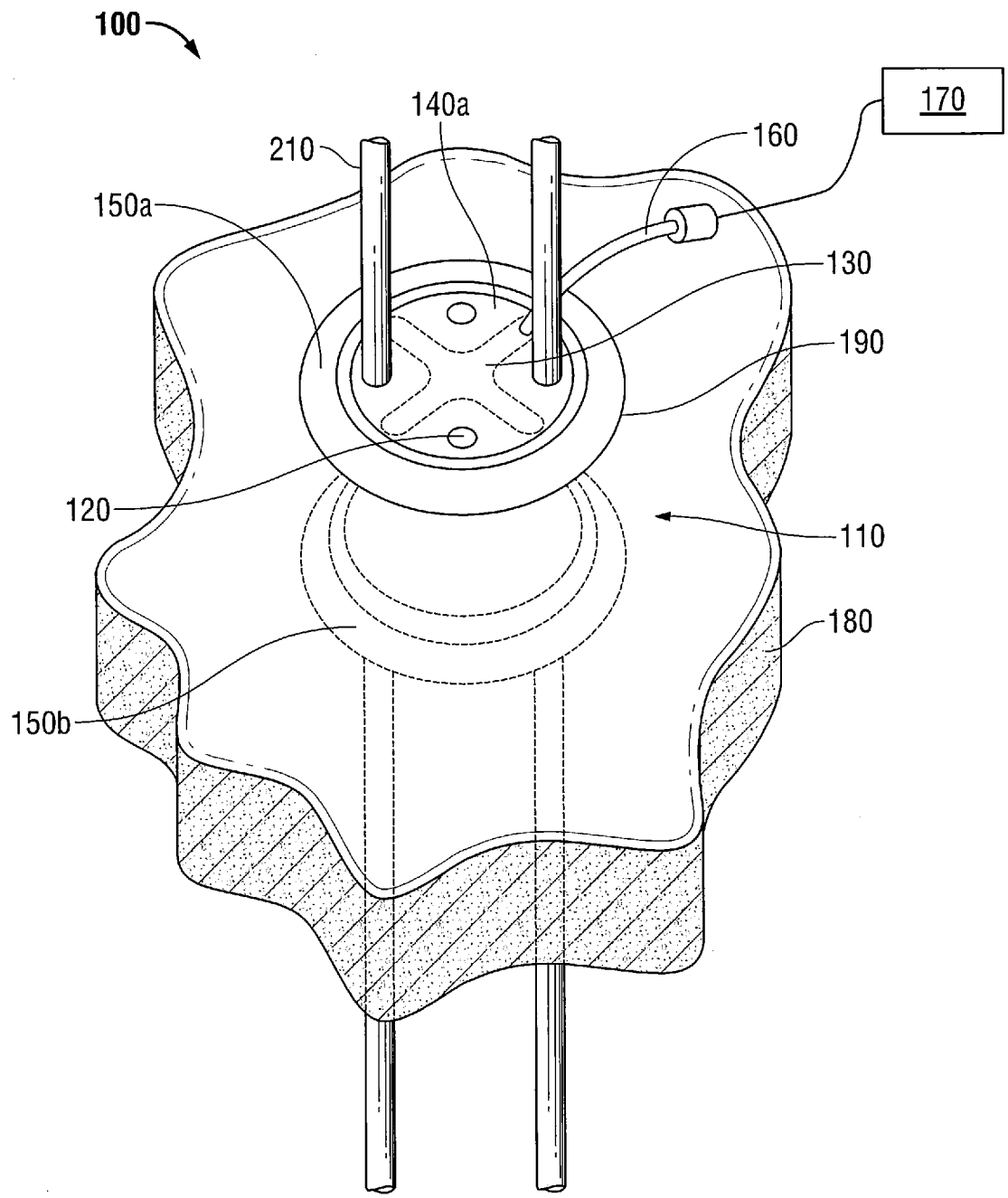
FIG. 3 is a top perspective view of the surgical access port shown in FIG. 1, in a first state and inserted into tissue through an incision site, having an inflation coupling and two surgical instruments disposed within two of the lumens.

Referring to FIG. 3, the surgical access port 100 is shown in top perspective view inserted into tissue 180 through an incision site 190. The proximal end 140a of the cylindrical member 110 can be seen extending through the surface of the tissue 180. In this arrangement, surgical instruments 210 can be inserted into lumens 120, and can be seen extending therethrough as shown in phantom view. Also shown in phantom view is the internal inflation cavity 130. Extending through the top of the proximal end 140a of cylindrical member 110 is inflation coupling 160. Thus, the surgical access port 100 in FIG. 3 is shown in a first, unexpanded, state.

Turning to FIG. 4, a side view of the surgical access port of 100 is shown. In this view, the surgical instruments 210 can be seen extending completely through the lumens 120 (shown in phantom view). Also shown is a relative spacing measurement X1, measured transverse to the longitudinal axis A1 between the centers of lumens 120, while the surgical access port 100 is in a first, unexpanded, state.

In use, the operator of the surgical access port 100 will first place the surgical access port 100 in an incision site 190 such that the surgical access port is disposed within a layer of tissue 180, as shown in FIG. 3. The operator of the surgical access port 100 will then couple the inflation coupling 160 to the source of inflation fluid 170, allowing the internal inflation cavity 130 to expand when fluid is introduced to the internal inflation cavity 130. The source of inflation fluid 170 supplies pressurized fluid to expand the internal inflation cavity 130. This may be accomplished by pumps or reservoirs, or any other suitable pressure-generating apparatus. The operator of the surgical access port 100 will allow the internal inflation cavity 130 to expand such that the walls of the cylindrical member 110 expand to fill the space between the cylindrical member 110 and the walls of the incision site 190, until a substantially fluid-tight seal is formed between the walls of the cylindrical member 110 and the walls of the incision site 190. The surgical access port 100 is then ready for surgical instruments and tools 210 to be inserted therethrough for use in minimally invasive surgical procedures.

Figure 5:
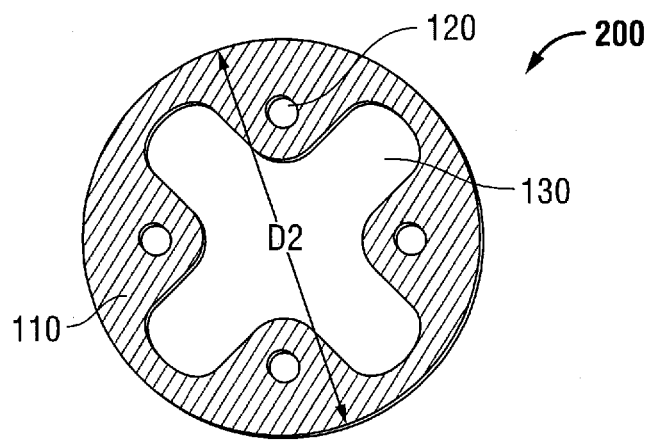
FIG. 5 is a top plan cross-sectional view along the line 2-2 of the surgical access port as shown in FIG. 2, in a second state and showing a corresponding second state diameter.

Referring now to FIG. 5, a cross-sectional view along the line 2-2 as shown in FIG. 2 is shown, now with the surgical access port 100 in an expanded, second state. Here, the second state diameter D2 is shown, clearly different than first state diameter D1. It is also shown that internal inflation cavity 130 has expanded and cylindrical member 110 has expanded in response.

Figure 6:
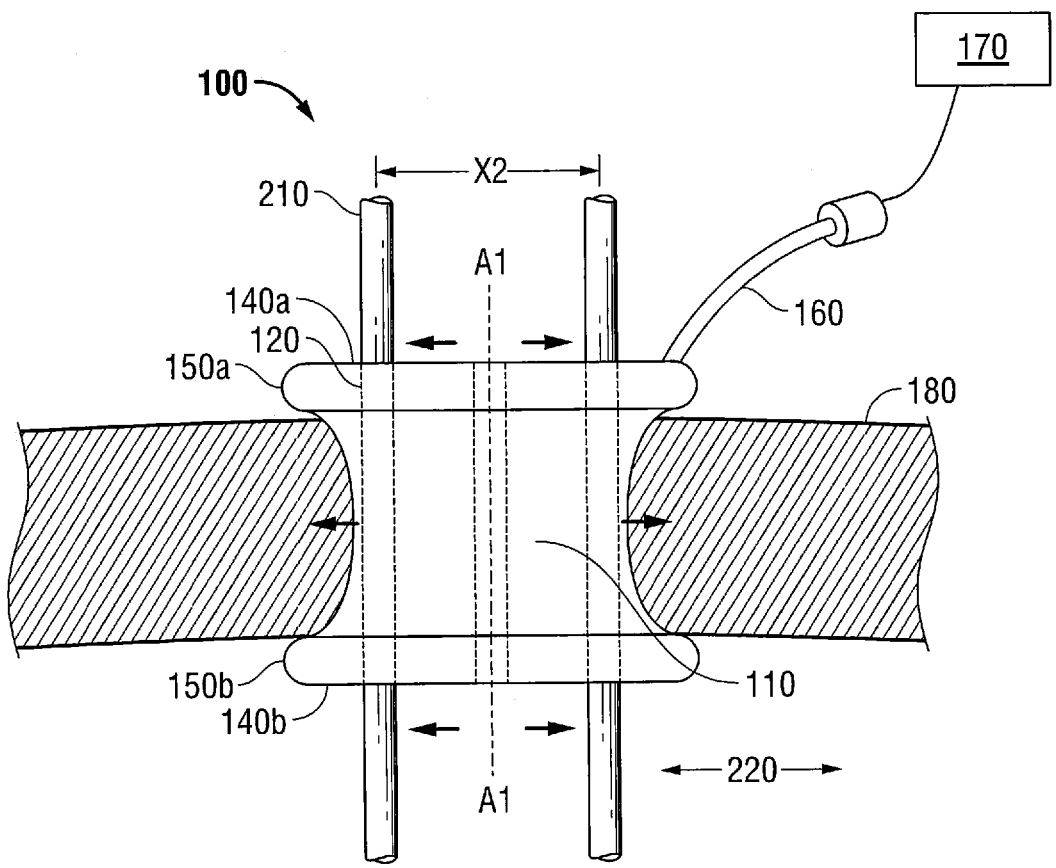
FIG. 6 is a side view of the surgical access port shown in FIG. 5 in an expanded second state and showing a corresponding increase in lumen spacing.

Turning to FIG. 6, the surgical access port 100 is in an expanded second state. The relative spacing measurement X2, measured transverse to the longitudinal axis between the centers of lumens 120 (shown in phantom view) is clearly different than the relative spacing measurement of the first state, X1. As a result, the lumens 120 enjoy greater relative spacing and greater freedom of movement. This greater spacing may also provide access to point in an internal body cavity 220 that may have been accessible by the surgical instruments 210 while the surgical access port 100 was in the first state. Additionally, the forces exerted by the expanded surgical access port 100 may also serve to retract tissue outward from an incision site 190. Further, the compressible nature of the cylindrical member 110 may cause the lumens 120 to form a tighter seal about surgical instruments 210 disposed therethrough in the second state.

In order to remove the device, the operator of the surgical access port 100 will uncouple the source of inflation fluid 170 from the inflation coupling 160. Surgical instruments and tools 210 will then be removed from the lumens 120, and inflation fluid will be released from the internal inflation cavity 130. This latter step may include opening a plug, seal, or other port in order to release pressurized inflation fluid. The surgical access port 100 will then transition from a second state to a first state, with a corresponding decrease in diameter, measured transverse to the longitudinal axis A1. The surgical access port can then be easily removed from an incision site 180.

Figure 7:
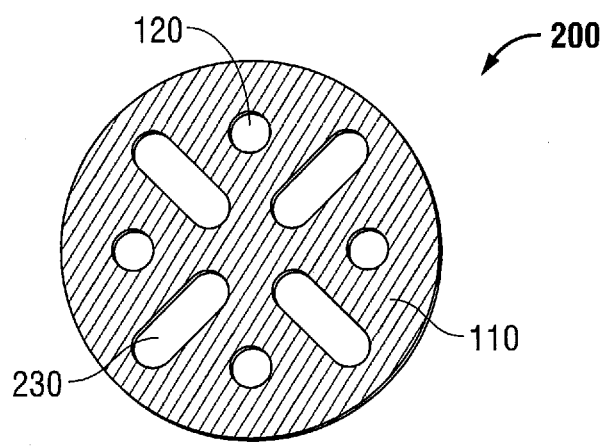
FIG. 7 is a top plan cross-sectional view of a surgical access port having four lumens and four separate internal inflation cavities in a first state.

Referring to FIG. 7, a surgical access port 200 is shown in a first state, with four lumens 120 spaced evenly about the longitudinal axis A1, as well as four separate inflation cavities 230, shown here evenly spaced about the longitudinal axis A1. Separate internal inflation cavities 230 may function to maximize spacing between lumens 120 upon transition of the surgical access port 200 from a first state to a second state.

It is additionally contemplated that the surgical access port may be coated with any number of medicating substances or materials to facilitate healing, or to make the use of the surgical access port during surgery more effective.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

What is claimed is:

1. A method of accessing an internal body cavity, comprising:
    positioning a surgical access port in an internal body cavity, the surgical access port including a cylindrical member having proximal and distal ends and defining a longitudinal axis, at least two lumens extending through the cylindrical member along the longitudinal axis, at least one cavity defined in the cylindrical member and positioned radially inwardly of the at least two lumens, and at least one source of inflation fluid coupled to the at least one cavity, the surgical access port having a first state with a corresponding first state diameter defined by the cylindrical member with the at least one cavity in an unexpanded state and a second state defined by the surgical access port with a corresponding second state diameter defined by the cylindrical member with the at least one cavity in an expanded state;
    supplying inflation fluid from the at least one source of inflation fluid to the at least one cavity such that the surgical access port expands from the first state to the second state, the second state diameter different than the first state diameter, and wherein in the first state, at least a portion of the at least one cavity extends linearly outward between two lumens of the at least two lumens, and in the second state, the two lumens are positioned at a greater radial distance from each other as compared to a radial distance therebetween in the first state; and
    accessing the internal body cavity via the surgical access port.

2. The method of claim 1, wherein accessing the internal body cavity includes introducing surgical instruments to the internal body cavity.

3. The method of claim 2, further including removing the surgical instruments.

4. The method of claim 1, wherein accessing the internal body cavity further includes performing a surgical operation.

5. The method of claim 4, further including retracting tissue at an incision site with the surgical access port in the second state.

6. The method of claim 5, further including removing the surgical access port from the incision site.

7. The method of claim 1, further including releasing the inflation fluid from the at least one cavity, thereby allowing the surgical access port to transition from the second state to the first state.

* * * * *